United States Patent
Kitano et al.

(10) Patent No.: US 11,629,454 B2
(45) Date of Patent: *Apr. 18, 2023

(54) METHOD FOR PRODUCING CHEMICALLY MODIFIED CELLULOSE FIBER

(71) Applicant: DAI-ICHI KOGYO SEIYAKU CO., LTD., Kyoto (JP)

(72) Inventors: Yuka Kitano, Kyoto (JP); Masayuki Hashimoto, Kyoto (JP)

(73) Assignee: DAI-ICHI KOGYO SEIYAKU CO., LTD., Kyoto (JP)

(*) Notice: Subject to any disclaimer, the term of this patent is extended or adjusted under 35 U.S.C. 154(b) by 471 days.

This patent is subject to a terminal disclaimer.

(21) Appl. No.: 16/644,371

(22) PCT Filed: Sep. 28, 2018

(86) PCT No.: PCT/JP2018/036172
§ 371 (c)(1),
(2) Date: Mar. 4, 2020

(87) PCT Pub. No.: WO2019/073810
PCT Pub. Date: Apr. 18, 2019

(65) Prior Publication Data
US 2021/0062406 A1    Mar. 4, 2021

(30) Foreign Application Priority Data

Oct. 10, 2017    (JP) .............................. JP2017-197175

(51) Int. Cl.
| | | |
|---|---|---|
| C08B 5/14 | (2006.01) | |
| C08J 7/14 | (2006.01) | |
| D06M 11/66 | (2006.01) | |
| D01F 2/24 | (2006.01) | |
| D01F 11/02 | (2006.01) | |
| D01D 5/42 | (2006.01) | |
| D06M 101/06 | (2006.01) | |

(52) U.S. Cl.
CPC ............. *D06M 11/66* (2013.01); *D01D 5/423* (2013.01); *D01F 2/24* (2013.01); *D01F 11/02* (2013.01); *D06M 2101/06* (2013.01); *D10B 2505/02* (2013.01); *D10B 2509/00* (2013.01)

(58) Field of Classification Search
CPC .... C08B 5/14; C08J 7/14; D01D 5/42; D01D 5/423; D01F 11/02; D06M 11/66
USPC ...................... 264/147, 340; 8/116.1; 536/59
See application file for complete search history.

(56) References Cited

U.S. PATENT DOCUMENTS

| | | | |
|---|---|---|---|
| 2005/0133180 A1* | 6/2005 | West ....................... | A61L 15/42 |
| | | | 162/158 |
| 2010/0286387 A1 | 11/2010 | Hashaikeh et al. | |
| 2021/0155716 A1* | 5/2021 | Pahimanolis ............. | C08B 5/14 |

FOREIGN PATENT DOCUMENTS

| | | |
|---|---|---|
| JP | 2007-92034 A | 4/2007 |
| JP | 2012-526156 A | 10/2012 |

OTHER PUBLICATIONS

International Search Report dated Dec. 18, 2018 in PCT/JP2018/036172 filed on Sep. 28, 2018.

* cited by examiner

*Primary Examiner* — Leo B Tentoni
(74) *Attorney, Agent, or Firm* — Oblon, McClelland, Maier & Neustadt, L.L.P.

(57) ABSTRACT

Provided is a method for producing a chemically modified cellulose fiber with which fibrillation can be performed along with sulfation reaction.

The method for producing a chemically modified cellulose fiber includes a step (a) of treating a cellulose fiber with sulfamic acid to allow a cellulose fine fiber which is a constituent of the cellulose fiber to react with the sulfamic acid, thereby substituting some of hydroxyl groups of cellulose with a substituent represented by a structural formula (1) below (where M represents a monovalent to trivalent cation), and a step (b) of performing fibrillation simultaneously with the step (a).

[Chem. 1]

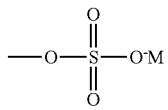

(1)

20 Claims, 1 Drawing Sheet

METHOD FOR PRODUCING CHEMICALLY MODIFIED CELLULOSE FIBER

TECHNICAL FIELD

The present invention relates to a method for producing a chemically modified cellulose fiber.

BACKGROUND ART

Cellulose fibers are used as industrial raw materials of food, cosmetics, functional paper, resin reinforcing materials, and the like. Furthermore, chemically modified cellulose fibers produced by chemically modifying surfaces of cellulose fibers have bright prospects because such chemically modified cellulose fibers are easily dispersed in water and thus are applicable to a wide range of industrial raw materials.

An example of chemically modified cellulose is sulfated cellulose. An example thereof is granular sulfated cellulose obtained by subjecting cellulose to sulfation by using sulfuric acid anhydride as a sulfating reagent (for example, Patent Literature 1). There is also disclosed a technique for producing sulfated cellulose having a degree of polymerization of 60 or less and having the cellulose II crystal structure by using an aqueous sulfuric acid solution as a sulfating reagent (for example, Patent Literature 2).

Hitherto, sulfuric acid anhydride having a high acidity or an aqueous sulfuric acid solution having a high concentration has been used as the sulfating reagent for subjecting cellulose to sulfation. However, neither sulfation with sulfamic acid nor fibrillating a cellulose fiber along with sulfation reaction is known.

CITATION LIST

Patent Literature

PTL 1: Japanese Unexamined Patent Application Publication No. 2007-92034
PTL 2: Japanese Unexamined Patent Application Publication (Translation of PCT Application) No. 2012-526156

SUMMARY OF INVENTION

Technical Problem

An object of an embodiment of the present invention is to provide a novel method for producing a sulfated cellulose fiber.

Solution to Problem

An embodiment of the present invention relates to a method for producing a chemically modified cellulose fiber, the method including steps (a) and (b) described below.
Step (a): A step of treating a cellulose fiber with sulfamic acid to allow a cellulose fine fiber which is a constituent of the cellulose fiber to react with the sulfamic acid, thereby substituting some of hydroxyl groups of cellulose with a substituent represented by a structural formula (1) below:

[Chem. 1]

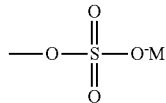

(1)

(where M represents a monovalent to trivalent cation.)
Step (b): A step of performing fibrillation simultaneously with the step (a)

Advantageous Effects of Invention

According to the present embodiment, a sulfated cellulose fiber having a cellulose I crystal structure can be provided. In addition, the sulfated cellulose fiber can be produced by performing fibrillation simultaneously with sulfation reaction, which is industrially advantageous.

DESCRIPTION OF EMBODIMENTS

Figure 1:
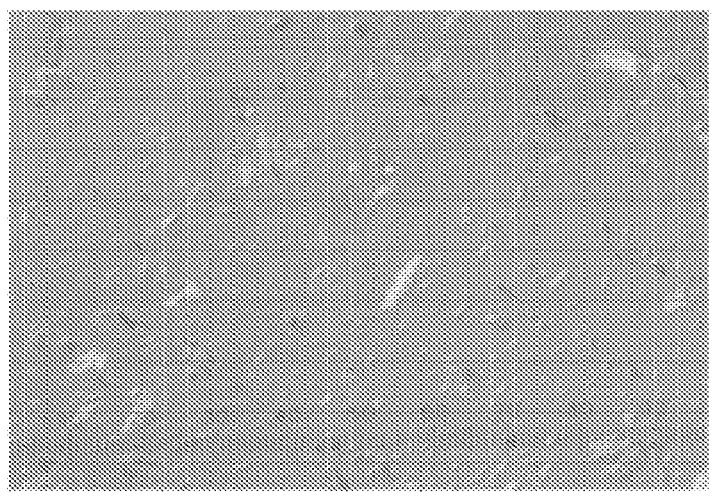
FIG. 1 is an optical micrograph (magnification: 100) of chemically modified cellulose fibers after a chemical modification step, the chemically modified cellulose fibers being obtained in Example 1.

A method for producing a chemically modified cellulose fiber according to the present embodiment includes a step (a): a step (chemical modification step) of treating a cellulose fiber with sulfamic acid to sulfate the cellulose fiber; and a step (b): a step (fibrillation step) of performing fibrillation simultaneously with the chemical modification step of the step (a).

[Cellulose Fiber]

Specific examples of cellulose fibers (that is, cellulose raw material) used in the chemical modification step include cellulose fibers derived from origins such as plants (e.g., wood, cotton, bamboo, hemp, jute, kenaf, agricultural land residual wastes, cloth, pulp, regenerated pulp, and wastepaper); animals (e.g., sea squirt); algaes; microorganisms (e.g., *acetobacter*); and microorganism products. Of these, pulp derived from plants is a preferred raw material.

The pulp is preferably chemical pulp (kraft pulp (KP) or sulfite pulp (SP)), semi-chemical pulp (SCP), chemiground pulp (CGP), chemimechanical pulp (CMP), groundwood pulp (GP), refiner mechanical pulp (RMP), thermomechanical pulp (TMP), or chemithermomechanical pulp (CTMP), which can be produced by chemical or mechanical pulping or combination of chemical and mechanical pulping of a plant raw material.

The cellulose fibers may be chemically modified within a range that does not impair the object of the present embodiment. That is, chemically modified pulp may be used as the cellulose fibers. The cellulose fibers can include, for example, an esterified product in which some or most of hydroxyl groups present on the surface of a cellulose fiber or on the surface of a cellulose fine fiber are converted to an acetic acid ester or a nitric acid ester; an etherified product in which some or most of hydroxyl groups present on the surface of a cellulose fiber or on the surface of a cellulose fine fiber are converted to methyl ether, hydroxyethyl ether, hydroxypropyl ether, hydroxybutyl ether, carboxymethyl ether, or cyanoethyl ether; or TEMPO-oxidized pulp in which primary hydroxyl groups are oxidized.

As the cellulose fibers, cellulose fibers having a cellulose I crystal and having a degree of cellulose I crystallinity of 50% or more are preferably used. The value of the degree of cellulose I crystallinity of the cellulose fibers is more preferably 60% or more, still more preferably 70% or more. The upper limit of the degree of cellulose I crystallinity of the cellulose fibers is not particularly limited but may be, for example, 98% or less, 95% or less, and 90% or less.

In this specification, the degree of crystallinity of cellulose refers to a degree of cellulose I crystallinity calculated by using the Segal method from diffraction intensity values determined by X-ray diffractometry, and is defined by the following equation.

$$\text{Degree of cellulose } I \text{ crystallinity } (\%) = [(I_{22.6} - I_{18.5})/I_{22.6}] \times 100$$

In the equation, $I_{22.6}$ represents a diffraction intensity of a lattice plane (002 plane) (diffraction angle $2\theta=$) 22.6°, and $I_{18.5}$ represents a diffraction intensity of an amorphous portion (diffraction angle $2\theta=18.5°$) in X-ray diffraction. Note that cellulose I refers to a crystal form of natural cellulose, and the degree of cellulose I crystallinity means a ratio of an amount of crystal region to a total amount of cellulose.

The form of the cellulose fibers used in the present embodiment is not particularly limited. However, from the viewpoint of handleability, the cellulose fibers preferably have a fiber form, a sheet form, a flocculent form, a powder form, a chip form, or a flake form.

The cellulose fibers used in the present embodiment preferably have an average degree of polymerization (that is, the number of repetitions of a glucose unit) of less than 350. When cellulose fibers having an average degree of polymerization of less than 350 are subjected to a chemical modification step described below, fibrillation that is performed simultaneously with the chemical modification step is facilitated while suppressing an increase in the viscosity after fibrillation. The average degree of polymerization of the cellulose fibers is more preferably 320 or less, still more preferably 300 or less. The lower limit of the average degree of polymerization of the cellulose fibers is not particularly limited and may be, for example, 100 or more, 150 or more, and 200 or more.

In this specification, the average degree of polymerization is a value measured by a viscosity method and can be specifically measured by the method described in Examples below.

In the case of using a cellulose raw material having an average degree of polymerization of 350 or more, a pretreatment is preferably performed prior to the reaction in the chemical modification step so that the average degree of polymerization becomes less than 350. The treatment method is not particularly limited, but a moderate degree of polymerization can be obtained by conducting, for example, an acid hydrolysis treatment, an enzyme treatment, or a mechanical treatment without decreasing the degree of crystallinity of the cellulose raw material. In the acid hydrolysis treatment, treatment conditions used are not limited. Examples of the acid hydrolysis treatment include methods using a mineral acid such as sulfuric acid, hydrochloric acid, or nitric acid. In the enzyme treatment, cellulase is used. In the mechanical treatment, the machine and treatment conditions used are not limited. Examples of the machine include shredders, ball mills, vibrating mills, stone mills, grinders, blenders, and high-speed rotary mixers.

[Chemical Modification Step/Fibrillation Step]

In the chemical modification step, the reaction between cellulose fibers and sulfamic acid (that is, sulfation reaction) can be conducted by immersing cellulose fibers in a chemical liquid that contains sulfamic acid.

In the present embodiment, it is preferable to perform fibrillation (that is, miniaturization) while chemically modifying, with sulfamic acid, the surfaces of cellulose fine fibers, which are constituents of cellulose fibers. That is, it is preferable to simultaneously perform a chemical modification step and a fibrillation step. Cellulose fibers are each formed of a bundle of cellulose fine fibers (also referred to as cellulose nanocrystals) which are constituents of the cellulose fibers. In the present embodiment, the surfaces of the cellulose fine fibers are preferably chemically modified with sulfamic acid while performing fibrillation, that is, loosening bundles without maintaining the shape of the cellulose fibers each of which is formed of a bundle of cellulose fine fibers. Since an esterification process is performed while fibrillating cellulose fine fibers in this manner, it is not necessary to perform a fibrillation process in the subsequent step, and thus efficiency and productivity can be improved.

The method for simultaneously performing the chemical modification step and the fibrillation step is not particularly limited. By using cellulose fibers having an average degree of polymerization of less than 350 as described above, the cellulose fibers can be fibrillated only by performing stirring during usual sulfation reaction, and thus it is not necessary to use a miniaturization process device such as a high-pressure homogenizer or a ball mill. The reason for this is probably as follows, although it is not necessarily clear. Since cellulose fibers having a low average degree of polymerization have short fiber lengths, the contact area between the fine fibers is small. Therefore, a repulsive force effect due to electric charge repulsion of sulfate groups is exhibited, and the cellulose fibers are easily fibrillated (however, it is not intended to limit the reason to this). Usually, in the case of using cellulose fibers having an average degree of polymerization of 350 or more, the viscosity of a cellulose fiber dispersion liquid is increased by fibrillation, and it becomes difficult to collect the resulting cellulose fibers. In contrast, in the case of using cellulose fibers having an average degree of polymerization of less than 350, the viscosity is low even after fibrillation, and the resulting cellulose fibers are settled by a centrifugal operation and can be collected in the form of a powder, which is good in terms of efficiency and productivity.

In the present embodiment, sulfamic acid is used as the sulfating reagent. Sulfamic acid has not only low solvency for cellulose but also low acidity compared with sulfuric acid anhydride, an aqueous sulfuric acid solution, and the like. Therefore, the degree of polymerization can be maintained, and the fiber length can be maintained. Furthermore, in contrast to sulfuric acid anhydride and an aqueous sulfuric acid solution, which are strongly acidic and have high corrosiveness, sulfamic acid neither has limitation in terms of handling nor is designated as a substance specified by the air pollution control law. Therefore, sulfamic acid has low load on the environment.

The amount of sulfamic acid used can be appropriately adjusted in consideration of the amount of the substituent introduced into cellulose fibers. Sulfamic acid can be used, for example, in an amount of preferably 0.01 to 50 moles, more preferably 0.1 to 30 moles per one mole of the anhydroglucose unit in cellulose molecules.

The chemical liquid used for conducting the sulfation reaction is a mixture of sulfamic acid and a solvent, and a catalyst may be further optionally added to the chemical liquid. Examples of the catalyst include urea, amides, and tertiary amines. From the industrial viewpoint, urea is preferably used. The amount of catalyst used is not particularly limited but is, for example, preferably 0.001 to 5 moles, more preferably 0.005 to 2.5 moles, still more preferably 0.01 to 2.0 moles per one mole of the anhydroglucose unit in cellulose molecules. A catalyst having a high concentration may be used without further treatment or may be diluted with a solvent in advance and then used. The method for adding the basic catalyst is not particularly limited. The catalyst may be added in a single operation, in batches, or on a continuous basis. These methods may be used in combination. However, it is preferable not to use a catalyst during the reaction from the viewpoint of environmental load and from the industrial viewpoint.

The solvent used in the chemical liquid is not particularly limited, and known solvents may be used. Examples of the known solvents include, besides water, linear or branched alcohols having 1 to 12 carbon atoms, such as methanol, ethanol, propanol, butanol, octanol, and dodecanol; ketones having 3 to 6 carbon atoms, such as acetone, methyl ethyl ketone, and methyl isobutyl ketone; linear or branched saturated hydrocarbons and unsaturated hydrocarbons having 1 to 6 carbon atoms; aromatic hydrocarbons such as benzene and toluene; halogenated hydrocarbons such as methylene chloride and chloroform; lower alkyl ethers having 2 to 5 carbon atoms; dioxane, acetonitrile, N,N-dimethylformamide, N,N-dimethylacetamide, dimethyl sulfoxide, N-methylpyrrolidone, and pyridine. These solvents may be used alone or as a mixture of two or more thereof. Of the above organic solvents, for example, water or a polar organic solvent is more preferred from the viewpoint of accelerating swelling of the cellulose raw material. The above solvents may be used alone or in combination of two or more thereof. The amount of solvent used is not particularly limited. For example, the solvent is used so that a solvent content of the cellulose fibers (that is, a ratio of the mass of the solvent to the dry mass of the cellulose fibers) is 10% by mass or more, preferably 10% by mass to 10,000% by mass, more preferably 20% by mass to 5,000% by mass, still more preferably 50% by mass to 2,000% by mass. With a decrease in the amount of solvent, the convenience of a washing step improves.

The temperature of the sulfation reaction is 0° C. to 100° C., preferably 10° C. to 80° C., more preferably 20° C. to 70° C. An excessively low reaction temperature is not preferred because it takes a long time to complete the reaction. An excessively high reaction temperature is not preferred because glycosidic bonds in cellulose molecules are cleaved. The sulfation reaction is usually completed within 30 minutes to five hours.

In order to obtain a product with less coloring, an inert gas such as nitrogen gas, neon gas, argon gas, or helium gas or carbon dioxide may be introduced during the sulfation reaction. The method for introducing the inert gas may be any of a method in which the reaction is performed while blowing the inert gas into a reaction vessel, a method in which the inside of a reaction vessel is purged with the inert gas prior to the reaction, the reaction vessel is then sealed, and the reaction is performed, and other methods. However, it is preferable not to use a gas during the reaction from the industrial viewpoint.

[Neutralization/Washing Step]

In the present embodiment, a step of neutralizing a sulfate salt may be performed as required. In the case where the pH of the resulting crude product of a sulfate salt decreases and the crude product becomes acidic, the crude product has low storage stability. Therefore, it is preferable to adjust the pH value to a neutral or alkaline range by adding a basic compound to the sulfate salt to perform neutralization. Examples of the basic compound used for neutralization include, but are not particularly limited to, alkali metal hydroxides, alkaline earth metal hydroxides, other inorganic salts, and amines. Specific examples thereof include sodium hydroxide, potassium hydroxide, calcium hydroxide, calcium acetate, calcium lactate, calcium oxalate, magnesium hydroxide, magnesium acetate, magnesium lactate, magnesium oxalate, basic aluminum lactate, basic aluminum chloride, ammonia, methylamine, dimethylamine, trimethylamine, triethylamine, monoethanolamine, diethanolamine, triethanolamine, and pyridine. In the present embodiment, one or more basic compounds can be used to perform neutralization.

In addition, a step of washing chemically modified cellulose fibers in a wet state may be performed for the purpose of terminating the reaction and/or removing a sulfating reagent residue, a residual catalyst, a solvent, and the like. In this case, washing conditions are not particularly limited, but the chemically modified cellulose fibers after the completion of the reaction are preferably washed by using an organic solvent.

The method for removing the solvent is not particularly limited but a centrifugal sedimentation method, filtration, pressing, or the like can be employed. Here, the organic solvent need not be completely removed so that a sheet formed of chemically modified cellulose fibers is left in the wet state with the organic solvent. An organic solvent content of the chemically modified cellulose fibers (that is, a ratio of the mass of the organic solvent to the dry mass of the chemically modified cellulose fiber aggregate) is preferably 1% by mass to 500% by mass, more preferably 10% by mass to 100% by mass, still more preferably 10% by mass to 50% by mass.

[Chemically Modified Cellulose Fiber]

Chemically modified cellulose fibers according to the present embodiment obtained by the production method described above are each a chemically modified cellulose fiber which has a cellulose I crystal and in which some hydroxyl groups in a glucose unit constituting cellulose are substituted with a substituent represented by a formula (1) below.

[Chem. 2]

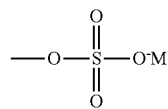

(1)

In the formula, M represents a monovalent to trivalent cation.

(Cellulose I Crystal)

The chemically modified cellulose fibers have a cellulose I crystal structure, and the degree of crystallinity thereof is preferably 50% or more. When the degree of crystallinity is 50% or more, characteristics derived from the cellulose crystal structure can be exhibited to improve thickening properties and mechanical strength. The degree of crystallinity is more preferably 60% or more, still more preferably 65% or more, and may be 70% or more. The upper limit of the degree of crystallinity is not particularly limited. From the viewpoint of improving the reaction efficiency of sulfation reaction, the degree of crystallinity is preferably 98% or less, more preferably 95% or less, still more preferably 90% or less, and may be 85% or less.

(Substituent)

The substituent represented by the formula (1) is a sulfate group. As shown by the formula below, the substituent has a structure in which, instead of a hydrogen atom, —SO$_3$⁻M is bound to an oxygen atom of a hydroxyl group in cellulose where the wavy line portion represents a cellulose molecule, and thus the sulfate group is introduced into a cellulose fiber.

[Chem. 3]

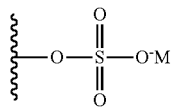

Examples of the monovalent to trivalent cation represented by M in the formula (1) include a hydrogen ion, metal ions, and ammonium ions. In the case of a divalent or trivalent cation, the cation forms ionic bonds between the cation and two or three —OSO$_3$⁻.

Examples of the metal ions include alkali metal ions, alkaline earth metal ions, transition metal ions, and other metal ions. Here, examples of the alkali metals include lithium, sodium, potassium, rubidium, and cesium. Examples of the alkaline earth metals include calcium and strontium. Examples of the transition metals include iron, nickel, palladium, copper, and silver. Examples of the other metals include beryllium, magnesium, zinc, and aluminum.

Examples of the ammonium ions include not only NH$_4$⁺ but also ammonium ions derived from various amines formed by replacing at least one hydrogen atom of NH$_4$⁺ with an organic group. Examples thereof include NH$_4$⁺, quaternary ammonium cations, alkanolamine ions, and a pyridinium ion.

The cation represented by M is preferably a sodium ion, a potassium ion, a calcium ion, or a quaternary ammonium cation from the viewpoint of storage stability. The cations listed above may be any one or a combination of two or more thereof.

(Amount of Substituent Introduced)

In the chemically modified cellulose fibers, an amount of the substituent represented by the formula (1) and introduced per 1 g of the chemically modified cellulose fibers is preferably 0.1 to 3.0 mmol. When the amount introduced is 3.0 mmol/g or less, the effect of maintaining the cellulose crystal structure can be enhanced. The amount introduced is more preferably 2.8 mmol/g or less, still more preferably 2.5 mmol/g or less, and may be 2.0 mmol/g or less, and 1.5 mmol/g or less. The amount introduced is preferably 0.1 mmol/g or more, more preferably 0.15 mmol/g or more, still more preferably 0.2 mmol/g or more from the viewpoint of covering, with the substituent, the entire surfaces of cellulose fine fibers which are constituents of cellulose fibers.

In this specification, the amount of substituent introduced is a value calculated by potentiometry. For example, a modifying agent used as a raw material and by-products such as a hydrolysate of the modifying agent are removed by washing, and subsequently, the amount of substituent can be calculated by potentiometric analysis. The amount of substituent can be specifically measured by the method described in Examples below.

(Average Degree of Polymerization)

The average degree of polymerization of the chemically modified cellulose fibers is preferably less than 350. When the average degree of polymerization is less than 350, fibrillation properties can be improved because, during fibrillation, the fibers can be dispersed without being entangled with each other. The average degree of polymerization is more preferably 320 or less, still more preferably 300 or less, and may be 250 or less. The lower limit of the average degree of polymerization is not particularly limited and may be, for example, 50 or more, 80 or more, 100 or more, and 150 or more.

(Average Fiber Width and Average Fiber Length)

The chemically modified cellulose fibers according to the present embodiment are fibers that are fibrillated along with chemical modification as described above. Therefore, the chemically modified cellulose fibers according to the present embodiment can be referred to as chemically modified fibrillated cellulose fibers or chemically modified cellulose fine fibers.

The average fiber width of the chemically modified cellulose fibers is not particularly limited as long as the average fiber width is smaller than that of the cellulose fibers before fibrillation and may be, for example, 20 μm or less, 10 μm or less, and 8 μm or less. The lower limit of the average fiber width is also not particularly limited and may be, for example, 3 nm or more, 5 nm or more, and 10 nm or more.

The average fiber length of the chemically modified cellulose fibers is not particularly limited and may be, for example, 500 μm or less, 300 μm or less, and 200 μm or less. The lower limit of the average fiber length is also not particularly limited and may be, for example, 0.1 μm or more, 0.3 μm or more, and 0.5 μm or more.

In this specification, the average fiber width and the average fiber length of chemically modified cellulose fibers are respectively the averages of fiber widths and fiber lengths of 50 fibers measured by microscopic observation and are specifically measured by the method described in Examples below.

[Operation and Effect/Use]

The chemically modified cellulose fibers according to the present embodiment have cellulose surfaces that have been subjected to sulfation and thus can be used as a thickener or a water-absorptive material. The chemically modified cellulose fibers can be used in, for example, industrial raw materials of food, cosmetics, functional paper, resin reinforcing materials, and the like, and various other applications.

The present embodiment is industrially advantageous in that sulfated cellulose fibers can be efficiently produced with environmental suitability at high productivity. In more detail, chemically modified cellulose fibers can be produced at a low cost while reducing the environmental load by allowing cellulose fibers and sulfamic acid to react with each other.

EXAMPLES

Hereafter, the present invention will be described in more detail by way of Examples. However, the present invention is not limited to the Examples.

Measurement/evaluation methods in Examples and Comparative Examples are as follows.

(1) Degree of Cellulose I Crystallinity

The X-ray diffraction intensities of cellulose fibers and chemically modified cellulose fibers were measured by X-ray diffractometry. The degree of cellulose I crystallinity was calculated from the measurement results by the following equation using the Segal method.

Degree of cellulose $I$ crystallinity (%)=[($I_{22.6}$−$I_{18.5}$)/ $I_{22.6}$]×100

In the equation, $I_{22.6}$ represents a diffraction intensity of a lattice plane (002 plane) (diffraction angle 2θ=) 22.6°, and $I_{18.5}$ represents a diffraction intensity of an amorphous portion (diffraction angle 2θ=18.5°) in X-ray diffraction. The X-ray diffraction intensities of samples were measured by using "RINT2200" manufactured by Rigaku Corporation under the following conditions.

X-ray source: Cu/Kα-radiation
Tube voltage: 40 kV
Tube current: 30 mA
Measurement range: diffraction angle 2θ=5° to 35°
X-ray scan speed: 10°/min (2) Identification of Chemically Modified Cellulose Fiber Groups (substituents) introduced in chemically modified cellulose fibers were identified with a Fourier transform infrared spectrophotometer (FT-IR, ATR method).

(3) Measurement of Amount of Substituent Introduced in Chemically Modified Cellulose Fiber The amount of substituents (sulfate groups) introduced was calculated by potentiometry. More specifically, 60 mL of a water dispersion of chemically modified cellulose fibers, the water dispersion having an adjusted solid content of 0.5% by mass, was prepared from a chemically modified cellulose fiber sample whose dry weight had been precisely weighed. The pH of the water dispersion was adjusted to about 2.5 with a 0.1 M aqueous hydrochloric acid solution. Subsequently, the resulting dispersion was filtered, and the fibers were washed with water. The fibers were again dispersed in 60 mL of water, and the pH of the resulting slurry was adjusted to about 11 by adding dropwise a 0.1 M aqueous potassium hydroxide solution. For this slurry, potentiometric titration was conducted by adding dropwise a 0.1 M aqueous hydrochloric acid solution. The amount of sulfate groups introduced in the chemically modified cellulose fibers was calculated from the amount of the 0.1 M aqueous hydrochloric acid solution added dropwise until the end point of the titration.

(4) Measurement of Average Degree of Polymerization of Cellulose Fiber and Chemically Modified Cellulose Fiber (Viscosity Method)

The average degrees of polymerization of cellulose fibers (before chemical modification) and chemically modified cellulose fibers were calculated by a viscosity method. The limiting viscosity number [η] was measured in accordance with JIS-P8215, and the average degree of polymerization (DP) was determined by the following equation.

DP=(1/Km)×[η]

(Km represents a coefficient and is a value specific to cellulose. 1/Km=156)

(5) Measurement of Average Fiber Width and Average Fiber Length of Chemically Modified Cellulose Fiber The average fiber width and the average fiber length of chemically modified cellulose fibers were measured with a scanning electron microscope (SEM). Wet chemically modified cellulose fibers were filtered to remove a solvent. Thus, a chemically modified cellulose fiber sheet was prepared. The chemically modified cellulose fiber sheet was freeze-dried in liquid nitrogen and observed with the SEM. The averages of fiber widths and fiber lengths of 50 fibers observed at a magnification of 100 to 10,000 were calculated and defined as the average fiber width and the average fiber length, respectively.

(6) Evaluation of Fiber Shape of Chemically Modified Cellulose Fiber

The shape of chemically modified cellulose fibers was evaluated by observation with an optical microscope in accordance with the following criteria.

A: Fibrillated.
B: A non-fibrillated portion remains.
C: The fiber shape is not maintained, and the fibers are dissolved or shortened.
D: Not fibrillated at all.

Example 1

In a separable flask equipped with a stirring blade, 0.5 g of sulfamic acid and 10 g of N,N-dimethylformamide (DMF) were placed, and stirring was performed for 10 minutes. Subsequently, 1.0 g of microcrystalline cellulose (manufactured by Merck KGaA, microcrystalline cellulose) was placed as cellulose fibers at room temperature. Here, the amount of sulfamic acid used as a sulfating reagent was 0.82 moles per one mole of the anhydroglucose unit in cellulose molecules. The resulting mixture was allowed to react by stirring (40 rpm) at 50° C. for three hours and then cooled to room temperature. Next, the resulting chemically modified cellulose fibers were taken out and placed in a 2 N aqueous sodium hydroxide solution serving as a neutralizer to adjust the pH to 7.6, and the reaction was terminated. The resulting chemically modified cellulose fibers were washed with water two to three times and then centrifuged. Thus, a water dispersion of the chemically modified cellulose fibers was prepared (amount of solid: 0.95 g, solid content: 8.1% by mass).

Example 2

The reaction, the washing, and the solvent removal process were performed as in Example 1 except that, in Example 1, the amount of sulfamic acid charged in the chemical modification step was 1.0 g, the amount of DMF charged was 8.0 g, the reaction conditions were changed to 25° C. and 24 hours, and no neutralizer was used.

Example 3

The reaction, the washing, and the solvent removal process were performed as in Example 1 except that, in Example 1, the amount of sulfamic acid charged in the chemical modification step was 1.5 g, 0.5 g of urea was added as a catalyst, the amount of DMF charged was 15 g, the reaction conditions were changed to 60° C. and three hours, and monoethanolamine was used as a neutralizer.

Example 4

The reaction, the washing, and the solvent removal process were performed as in Example 1 except that, in Example 1, the amount of sulfamic acid charged in the chemical modification step was 1.0 g, 0.5 g of pyridine was added as a catalyst, the reaction conditions were changed to 60° C. and five hours, and pyridine (the cation of which becomes a pyridinium ion) was used as a neutralizer.

Example 5

In a separable flask equipped with a stirring blade, 2.0 g of softwood kraft pulp (NBKP) and 100 mL of a 40% aqueous sulfuric acid solution were placed, and stirring was performed at 50° C. for 24 hours. After the reaction, the resulting reaction product was subjected to suction filtration and washed with water three times. Subsequently, the product was dried at 60° C. for 24 hours under reduced pressure and pulverized (at 16,000 rpm for one minute) by a blender treatment (Hi-Power Blender MX-1200X™, manufactured by Waring Commercial). Thus, 1.5 g of microcrystalline cellulose was prepared. In a separable flask equipped with a stirring blade, 0.5 g of sulfamic acid and 10 g of N,N-dimethylformamide (DMF) were placed, and stirring was performed for 10 minutes. Subsequently, 1.0 g of the microcrystalline cellulose derived from NBKP and prepared as described above was placed as cellulose fibers at room temperature. Here, the amount of sulfamic acid used as a sulfating reagent was 0.82 moles per one mole of the anhydroglucose unit in cellulose molecules. The resulting mixture was allowed to react by stirring (40 rpm) at 50° C. for three hours and then cooled to room temperature. Next, the resulting chemically modified cellulose fibers were taken out and placed in a 2 N aqueous sodium hydroxide solution serving as a neutralizer to adjust the pH to 7.6, and the reaction was terminated. The resulting chemically modified cellulose fibers were washed with water two to three times and then centrifuged. Thus, a water dispersion of the chemically modified cellulose fibers was prepared (amount of solid: 0.95 g, solid content: 8.1% by mass).

Comparative Example 1

The reaction, the washing, and the solvent removal process were performed as in Example 1 except that, in Example 1, 1.5 g of sulfur trioxide was used instead of sulfamic acid in the chemical modification step, the amount of DMF charged was 15 g, and the reaction conditions were changed to 50° C. and five hours.

Comparative Example 2

As cellulose fibers, 1.0 g of microcrystalline cellulose (manufactured by Merck KGaA, microcrystalline cellulose) was dispersed in water, and the resulting dispersion was diluted so as to have a solid content of 5.0% by mass. The resulting cellulose fiber water dispersion liquid was subjected to centrifugal separation. Thus, a water dispersion of cellulose fibers was prepared.

With regard to Examples and Comparative Examples described above, calculations of the degree of crystallinity and the average degree of polymerization were performed for the cellulose fibers before chemical modification, and identification of the group introduced, calculations of the amount of group introduced, the average degrees of polymerization, the average fiber width, the average fiber length, and the degree of crystallinity, and evaluation of the fiber shape were performed for the chemically modified cellulose fibers after the chemical modification step. The results are shown in Table 1.

Figure 2:
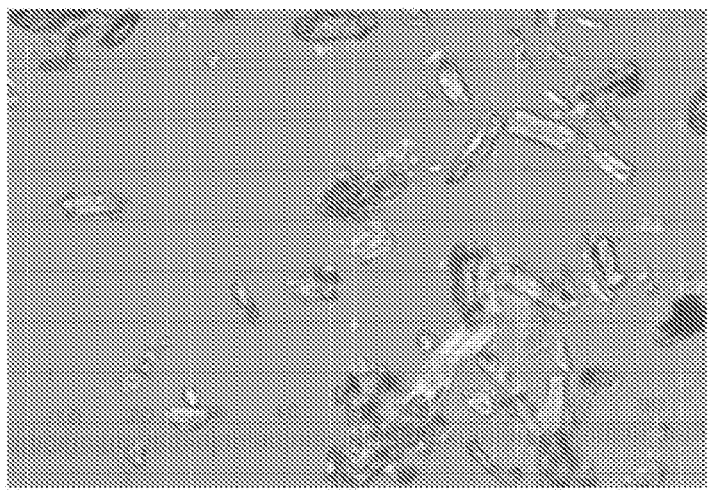
FIG. 2 is an optical micrograph (magnification: 100) of cellulose fibers before a chemical modification step in Comparative Example 1.

FIG. 1 (magnification: 100) is an optical micrograph of the chemically modified cellulose fibers after the chemical modification step, the chemically modified cellulose fibers being obtained in Example 1. FIG. 2 (magnification: 100) is an optical micrograph of the cellulose fibers before the chemical modification step in Comparative Example 1.

TABLE 1

|  |  | Example 1 | Example 2 | Example 3 | Example 4 | Example 5 | Comparative Example 1 | Comparative Example 2 |
|---|---|---|---|---|---|---|---|---|
| Cellulose fiber | Type | Microcrystalline cellulose | Microcrystalline cellulose | Microcrystalline cellulose | Microcrystalline cellulose | Microcrystalline cellulose | Microcrystalline cellulose | Microcrystalline cellulose |
|  | Degree of crystallinity [%] | 88 | 88 | 88 | 88 | 88 | 88 | 88 |
|  | Average degree of polymerization | 280 | 280 | 280 | 280 | 170 | 280 | 280 |
|  | Amount charged [g] | 1.0 | 1.0 | 1.0 | 1.0 | 1.0 | 1.0 | 1.0 |
| Reaction solution | Sulfating reagent — Type | Sulfamic acid | Sulfamic acid | Sulfamic acid | Sulfamic acid | Sulfamic acid | Sulfur trioxide | — |
|  | Amount charged [g] | 0.5 | 1.0 | 1.5 | 1.0 | 0.5 | 1.5 | — |
|  | Catalyst — Type | — | — | Urea | Pyridine | — | — | — |
|  | Amount charged [g] | — | — | 0.5 | 0.5 | — | — | — |
|  | Solvent — Type | DMF | DMF | DMF | DMF | DMF | DMF | — |
|  | Amount charged [g] | 10 | 8 | 15 | 10 | 10 | 15 | — |
| Reaction condition | Temperature [° C.] | 50 | 25 | 60 | 60 | 50 | 50 | — |
|  | Time [h] | 3 | 24 | 3 | 5 | 3 | 5 | — |
| Post-treatment | Neutralizer — Type | NaOH | — | MEA | Pyridine | NaOH | — | — |
|  | Cationic species | $Na^+$ | $NH_4^+$ | $NH_3^+C_2H_4OH$ | $C_5H_5N^+H$ | $Na^+$ | — | — |
| Evaluation | Amount introduced [mmol/g] | 0.18 | 0.40 | 1.10 | 0.48 | 0.22 | 2.3 | 0 |
|  | Degree of crystallinity [%] | 86 | 81 | 74 | 76 | 85 | 78 | 88 |
|  | Average degree of polymerization | 270 | 260 | 230 | 240 | 150 | 160 | 280 |
|  | Average fiber width [nm] | 1100 | 980 | 600 | 2090 | 2200 | — | 35000 |
|  | Average fiber length [μm] | 5 | 3 | 1 | 4 | 4 | — | 90 |
|  | Evaluation of fiber shape | A | A | A | A | A | C | D |

Details of the components in the table are as follows.
DMF: dimethylformamide
NaOH: sodium hydroxide
MEA: monoethanolamine The results are shown in Table 1 and FIGS. 1 and 2. In Comparative Example 1, the average degree of polymerization was decreased by sulfur trioxide, which is strongly acidic, and the fiber shape of the cellulose fibers was not maintained, resulting in a decrease in the length of the fibers. In contrast, in Examples 1 to 5, the sulfate group represented by the formula (1) could be introduced on the surfaces of cellulose fine fibers. In addition, the sulfate group was introduced while the cellulose fine fibers had the cellulose I crystal structure and maintained high degree of crystallinity and high average degree of polymerization. Furthermore, even without using an environmentally toxic sulfating reagent such as sulfur trioxide, sulfation could be easily performed at a low cost by using a reagent having environmental suitability. Furthermore, since fibrillation is caused simultaneously with chemical modification, chemically modified cellulose fibers could be efficiently obtained at high productivity.

Some embodiments of the present invention have been described above. These embodiments are only exemplary and are not intended to limit the scope of the invention. These embodiments can be carried out in various other forms, and various omissions, replacements, and modifications may be made without departing from the spirit of the invention. These embodiments and omissions, replacements, modifications, and the like of the embodiments fall within the scope or spirit of the invention and also fall within the scope of the invention as defined by the appended claims and equivalents thereof.

The invention claimed is:

1. A method for producing a chemically modified cellulose fiber, comprising:
   treating a cellulose fiber with sulfamic acid such that a cellulose fine fiber which is a constituent of the cellulose fiber is allowed to react with the sulfamic acid and that some of hydroxyl groups of cellulose is substituted with a substituent of formula (1)

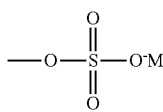
(1)

where M is a monovalent to trivalent cation; and
   performing fibrillation simultaneously with the treating of the cellulose fiber with the sulfamic acid.

2. The method of claim 1, wherein the treating of cellulose fiber with the sulfamic acid comprises treating the cellulose fiber having an average degree of polymerization of less than 350 with the sulfamic acid.

3. The method of claim 1, wherein the chemically modified cellulose fiber has a cellulose I crystal structure and the substituent substituting some of hydroxyl groups of cellulose in the chemically modified cellulose fiber such that an amount of the substituent is in a range of 0.1 to 3.0 mmol per 1 g of the chemically modified cellulose fiber, and the chemically modified cellulose fiber has an average degree of polymerization of less than 350.

4. The method of claim 2, wherein the chemically modified cellulose fiber has a cellulose I crystal structure and the substituent substituting some of hydroxyl groups of cellulose in the chemically modified cellulose fiber such that an amount of the substituent is in a range of 0.1 to 3.0 mmol per 1 g of the chemically modified cellulose fiber, and the chemically modified cellulose fiber has an average degree of polymerization of less than 350.

5. The method of claim 1, wherein the treating of cellulose fiber with the sulfamic acid comprises treating the cellulose fiber having an average degree of polymerization of less than 320 with the sulfamic acid.

6. The method of claim 1, wherein the treating of cellulose fiber with the sulfamic acid comprises treating the cellulose fiber having an average degree of polymerization of less than 300 with the sulfamic acid.

7. The method of claim 1, wherein the treating of cellulose fiber with the sulfamic acid comprises treating the cellulose fiber having an average degree of polymerization in a range of 100 to 350 with the sulfamic acid.

8. The method of claim 1, wherein the treating of cellulose fiber with the sulfamic acid comprises treating the cellulose fiber having an average degree of polymerization in a range of 150 to 320 with the sulfamic acid.

9. The method of claim 1, wherein the treating of cellulose fiber with the sulfamic acid comprises treating the cellulose fiber having an average degree of polymerization in a range of 200 to 300 with the sulfamic acid.

10. The method of claim 1, wherein the chemically modified cellulose fiber has an average degree of polymerization of less than 320.

11. The method of claim 1, wherein the chemically modified cellulose fiber has an average degree of polymerization of less than 300.

12. The method of claim 1, wherein the chemically modified cellulose fiber has an average degree of polymerization of less than 250.

13. The method of claim 1, wherein the chemically modified cellulose fiber has an average degree of polymerization in a range of 50 to 350.

14. The method of claim 1, wherein the chemically modified cellulose fiber has an average degree of polymerization in a range of 80 to 320.

15. The method of claim 1, wherein the chemically modified cellulose fiber has an average degree of polymerization in a range of 100 to 300.

16. The method of claim 1, wherein the chemically modified cellulose fiber has an average degree of polymerization in a range of 150 to 250.

17. The method of claim 1, wherein the chemically modified cellulose fiber has a cellulose I crystal structure and the substituent substituting some of hydroxyl groups of cellulose in the chemically modified cellulose fiber such that an amount of the substituent is in a range of 0.15 to 2.8 mmol per 1 g of the chemically modified cellulose fiber, and the chemically modified cellulose fiber has an average degree of polymerization of less than 350.

18. The method of claim 1, wherein the chemically modified cellulose fiber has a cellulose I crystal structure and the substituent substituting some of hydroxyl groups of cellulose in the chemically modified cellulose fiber such that an amount of the substituent is in a range of 0.2 to 2.5 mmol per 1 g of the chemically modified cellulose fiber, and the chemically modified cellulose fiber has an average degree of polymerization of less than 350.

19. The method of claim 1, wherein the chemically modified cellulose fiber has a cellulose I crystal structure and the substituent substituting some of hydroxyl groups of cellulose in the chemically modified cellulose fiber such that an amount of the substituent is in a range of 0.2 to 2.0 mmol per 1 g of the chemically modified cellulose fiber, and the chemically modified cellulose fiber has an average degree of polymerization of less than 350.

20. The method of claim 1, wherein the chemically modified cellulose fiber has a cellulose I crystal structure and the substituent substituting some of hydroxyl groups of cellulose in the chemically modified cellulose fiber such that an amount of the substituent is in a range of 0.2 to 1.5 mmol per 1 g of the chemically modified cellulose fiber, and the chemically modified cellulose fiber has an average degree of polymerization of less than 350.

\* \* \* \* \*